United States Patent [19]
Henry et al.

[11] Patent Number: 5,741,254
[45] Date of Patent: Apr. 21, 1998

[54] IMPLANT FOR AN OSTHEOSYNTHESIS DEVICE, IN PARTICULAR FOR THE SPINE

[75] Inventors: Patrick Henry; Philippe Lapresle, both of Neuilly-Sur-Seine; Gilles Missenard, Paris, all of France

[73] Assignee: Stryker Corporation, Kalamazoo, Mich.

[21] Appl. No.: 535,279

[22] PCT Filed: Apr. 18, 1994

[86] PCT No.: PCT/FR94/00435

§ 371 Date: Oct. 19, 1995

§ 102(e) Date: Oct. 19, 1995

[87] PCT Pub. No.: WO94/23660

PCT Pub. Date: Oct. 27, 1994

[30] Foreign Application Priority Data

Apr. 19, 1993 [FR] France ................. 93 04584

[51] Int. Cl.⁶ ................................ A61B 17/70
[52] U.S. Cl. ................. 606/61; 606/60; 606/64; 606/72; 606/73
[58] Field of Search ............... 606/61, 60, 64, 606/72, 73

[56] References Cited

U.S. PATENT DOCUMENTS

| | | | |
|---|---|---|---|
| 5,190,543 | 3/1993 | Schlapfer | 606/61 |
| 5,380,325 | 1/1995 | Lahille et al. | 606/61 |

FOREIGN PATENT DOCUMENTS

| | | |
|---|---|---|
| 509 322 A1 | 10/1992 | European Pat. Off. . |
| 2656214 | 6/1991 | France . |
| 2834891 | 1/1980 | Germany . |
| 408381 | 2/1966 | Switzerland . |
| 2033758 | 5/1980 | United Kingdom . |

Primary Examiner—Michael Buiz
Assistant Examiner—Daphna Shai
Attorney, Agent, or Firm—Roylance, Abrams, Berdo & Goodman, L.L.P.

[57] ABSTRACT

An implant for an ostheosynthesis device, in particular for the spine, comprises an anchoring portion (11) for anchoring to bone and a body in which a channel (13) is formed suitable for receiving a rod (T), the channel opening out sideways in the body, a hollow element (20) suitable for surrounding the body (12) and possessing two notches suitable for receiving the rod on either side of the body (12), and a screw (30) for fixing the hollow element on the body. According to the invention: the hollow element is a cover (20) fitting over the body with a rounded top portion (21b) in which an opening (25) is formed, the body (12) includes a tapped hole (14) facing said opening, and the head (31) of a screw (30) bears against the top (21b, 25a) of the cover, its threaded portion (32) being screwed in the tapped hole through said opening.

16 Claims, 1 Drawing Sheet

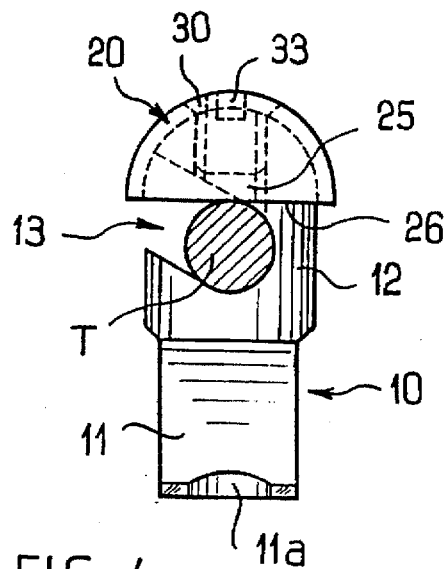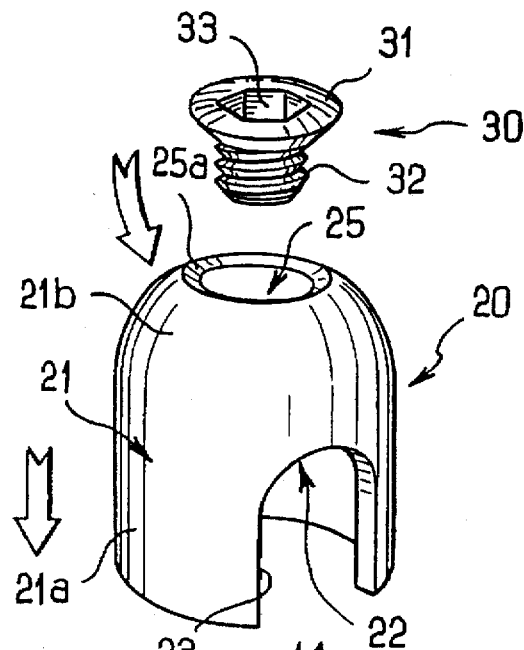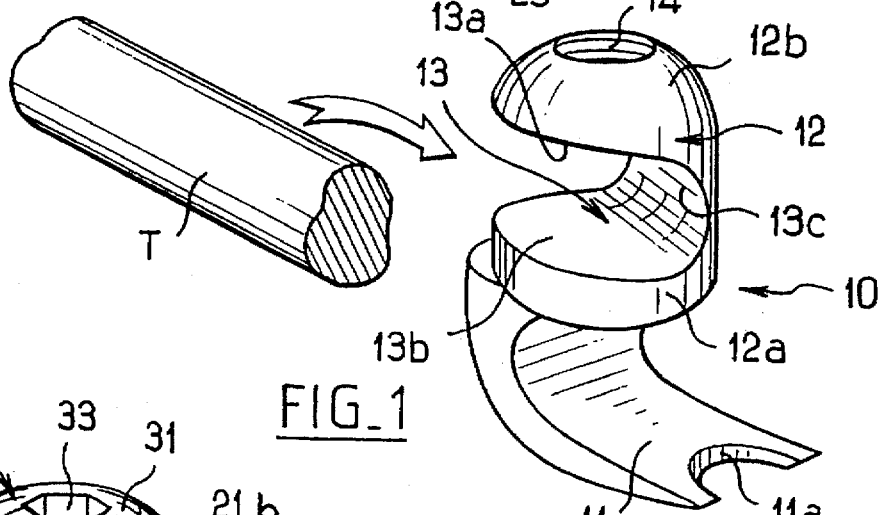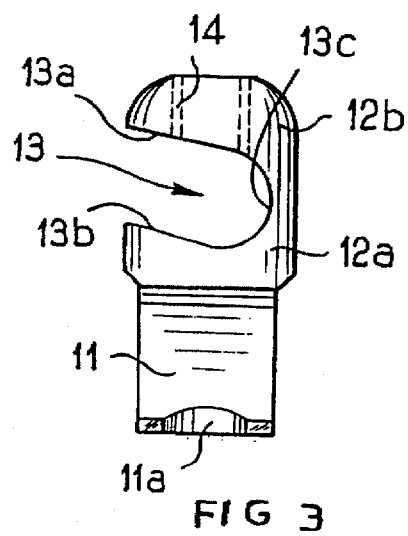

IMPLANT FOR AN OSTHEOSYNTHESIS DEVICE, IN PARTICULAR FOR THE SPINE

The present invention relates to the field of implants for ostheosynthesis, in particular for the spine, and more particularly it relates to an implant for an ostheosynthesis device, in particular for the spine, of the type comprising an anchoring portion for anchoring to bone and a body in which a channel is formed suitable for receiving a rod, the channel opening out sideways in the body, a hollow element suitable for surrounding the body and possessing two notches suitable for receiving the rod on either side of the body, and means for fixing the hollow element on the body.

Document EP-A-0 517 059 teaches an implant of that type.

Nevertheless, that known implant suffers from a certain number of drawbacks. Firstly, it is relatively bulky because the body of the implant possesses a threaded extension extending backwardly, with the fixing means consisting in a nut of relatively large dimensions screwed onto the extension. In addition, by its very nature, the nut has projecting angles which are generally undesirable for implants since they damage the environment.

Also, nut tightening generally needs to be performed with an extremely large amount of torque, and as a result during tightening there is a risk of metal particles being torn off and released from the threads of the nut and/or the threaded extension, thus running the risk of metallosis developing in the patient.

The present invention seeks to mitigate or at least to attenuate all those drawbacks of the prior art.

To this end, it proposes an implant of the type mentioned in the introduction and characterized in that:

the hollow element is constituted by a cover fitting over the body and having a rounded top portion in which an opening is formed;

the body including a tapped hole facing said opening; and the fixing means comprising a screw having a head that bears against the top portion of the cover and a threaded portion that is screwed in the tapped hole.

Advantageously, going from the outside towards the center of the body, the channel slopes towards the bone anchoring portion.

In a preferred embodiment, the body has a top portion that is substantially hemispherical in shape and the cover has a top portion that is of complementary substantially hemispherical shape; then preferably, the head of the screw has an outside surface that extends the rounded top surface of the cover with continuity.

In the same spirit, the invention also provides an implant for an ostheosynthesis device, in particular for the spine, of the type comprising an anchoring portion for anchoring to bone and a body in which a channel is formed suitable for receiving a rod, the channel opening out sideways in the body, a hollow element fixed on the body to hold the rod in the channel, and means for fixing the hollow element on the body, the implant being characterized in that:

going from the outside towards the center of the body, the channel slopes towards the bone anchoring portion; and the hollow element fits over the body and possesses a rounded top portion terminated by a generally flat edge bearing against the rod at either end of the channel to lock said rod in the channel, an opening being formed in said top portion;

the body including a tapped hole facing said opening; and the fixing means comprising a screw having a head that bears against the top portion of the hollow element and a threaded portion that is screwed in the tapped hole.

Advantageously, the body has a top portion that is substantially hemispherical in shape and the hollow element comprises a cap that is of complementary substantially hemispherical shape.

Then preferably, the head of the screw has an outside surface that extends the rounded top surface of the cap with continuity.

Finally, it is appropriate for the screw to be mounted in unloseable manner in the opening of the hollow element.

Other aspects, objects, and advantages of the present invention appear more clearly on reading the following detailed description of preferred embodiments thereof given by way of example and made with reference to the accompanying drawing, in which:

FIG. 1 is an exploded perspective view of an implant of the invention and an associated rod;

FIG. 2 is a perspective view of the implant and the rod in the assembled state;

FIG. 3 is an elevation view from the side of a portion of the implant; and

FIG. 4 is an elevation view from the side of an implant constituting a variant embodiment of the invention.

With reference to the drawing, there can be seen an implant for ostheosynthesis of the spine which comprises a first element 10 for anchoring to bone and a body 12 for fixing the element 10 to a rod T.

The anchoring portion 11 is implemented in this case in the form of a curved pedicle hook with the edge of its free end possessing a notch 11a in conventional manner.

The body 12 formed integrally with the hook 11 has a generally cylindrically shaped outline in a base region 12a extending from the hook 11. Remote from the hook it is terminated by a top region 12b which is generally hemispherical in shape.

A channel 13 is formed in the base portion 12a of the body 12 to receive the rod T. The channel opens out generally sideways and its height is slightly greater than the diameter of the rod T.

As can be seen in particular in FIG. 3, the channel 13 has a slight downwards slope going from the outside towards the center of the body 12, and it is defined by a top wall 13a and a bottom wall 13b that are parallel to each other and that provide the above-mentioned slope, and also by an end wall 13c that is generally semi-cylindrical.

The channel extends across the entire width of the body 12 and the rod T can be inserted sideways therein until it reaches the end, the end and the rod being complementary in shape.

The body 12 also possesses a tapped hole 14 which extends downwards along the axis of the body from the top region 12b of its hemispherical free end.

In the present example, the tapped hole passes through the top wall 13a of the channel 13, however in a variant it could be a blind hole open only to the top of the body 12.

The implant of the invention also comprises a cover or cap 20 suitable for fitting over the body 12 having the rod T installed in its channel 15. The cover has a wall 21 with a base region 21a which is generally circularly cylindrical and a top region 21b which is generally hemispherical in shape. The cover 20 defines an inside cavity 22 whose shape, at least in cross-section, is identical to the outside shape of the body 12, so as to be capable of fitting thereover with as little transverse play as possible, while nevertheless not impeding easy sliding between the body 12 and the cover 20 while the cover is being put into place.

Wall portion 21a has two generally U-shaped notches 23 in two diametrically opposite regions, only one notch being visible in FIGS. 1 and 2, which notches extend parallel to the axis of the cover (vertically in the figures). Each notch extends upwards from the bottom edge of the wall 21a over a length that is slightly longer than the diameter of the rod T and terminates at a well-defined height in a semicircular end so as to be complementary in shape to the top of the rod.

The top of the cover 20 has an opening 25 of diameter equal to or slightly greater than the diameter of the tapped hole 14 in the body 12. This opening has a peripheral chamfer referenced 25a.

Finally, the implant of the invention comprises a screw 30 having a head 31 and a threaded portion 32 complementary to the tapping formed in the body 12.

The bottom surface of the head 31 around the portion 32 is chamfered to match the chamfer 25a of the cover.

The shape of the top surface of the head 31 is that of a portion of a sphere having approximately the same radius as the outer spherical surface of the top portion 21b of the cover. Thus, when in place, the head 31 can be flush with the outside surface of the top portion 21b of the cover.

Also, it is advantageous for the thread of the screw 30 and the diameter of the opening 25 to be designed in such a manner as to ensure that the screw 30 can be held loose in said opening prior to assembly, so as to make the screw unloseable. This is advantageously achieved by giving the opening 25 a diameter that is slightly smaller than the overall outside diameter of the threads of the screw.

For the surgeon, this greatly simplifies the handling of the various portions of the implant.

In this top surface, there is formed a handling and tightening facility, in this case a six-sided hexagonal socket 33 for receiving the end of an "Allen" type key.

The various elements of the implant as described above are naturally made out of a material that is biocompatible, such as a titanium alloy or stainless steel.

The implant as described above is put into place as follows: firstly the anchoring portion 11 is placed on a vertebra in the usual manner so as to position the body 12 in the desired location. The rod T is then engaged sideways into the channel 13 until it engages the end thereof. It is important to observe at this point that the hemispherical shape of the top 12b of the body 12, and the slope of the channel 13 as indicated above serve to make this engagement easier to perform, particularly when the rod T has already been secured to one or more other implants. If the rod T is brought to the vicinity of the top of the implant and if it is then pushed down towards the side having the entrance to the channel 13, then the rod will slide progressively and without encountering any obstacle over the side of the body 12 and will then penetrate easily into the channel 13 as soon as it overlies it.

Thereafter, the cover 20 is put into place over the body 12 of the element 10 and over the rod T, with the rod being received in the two notches 23 at each of the diametrically opposite outlet ends of the channel, the notches being appropriately prepositioned for this purpose.

It will be observed that from this instant, the cover 20 is prevented from rotating by the rod T co-operating with the notches 23.

The screw is then engaged in the opening 25 and tightened in the tapping 14 by means of an appropriate tool, thereby securing the cover or cap 20 on the body 12 and holding the rod T firmly captive. It may be observed at this point that the end of each notch 23 is positioned so as to bear against the rod T before the end of the cavity 22 in the cover 20 comes to bear against the dome 12b of the body 12, so as to ensure that the rod is effectively locked.

After being assembled and locked, the implant is as shown in FIG. 2. It can be seen that there is practically no outwardly directed projecting angle. In particular, the head of the screw 30 extends the dome-shape surface of the cover in continuous manner. It can also be seen that the risks of particles of matter becoming dislodged during tightening of the screw at high torque exist almost solely in regions inside the implant, i.e. inside the tapped hole 14, thereby reducing the risks of metallosis.

FIG. 4 shows a variant embodiment of the invention. In this variant, the cover 20 comprises no more than a generally hemispherical wall that is complementary to the hemispherical region 12b of the body, and towards the anchoring portion 11 it is terminated in an annular flat edge 26.

When the cover 20 is secured to the body 12 by means of the screw 30, as described above, the edge 26 comes to bear on the rod T on either side of the channel 13 so as to lock said rod. In this variant, it is necessary for the channel to tilt substantially, as shown, in order to achieve satisfactory locking since the cover 20 no longer has the notches 23 of FIGS. 1 and 3 and it is only its edge 26 that opposes movement of the rod T out from the channel 13: the greater the inclination of the edge 26 relative to the escape direction of the rod from the channel, the more effective the opposition.

Naturally, the present invention is not limited to the embodiments described above and shown in the drawings, and the person skilled in the art will be able to apply any variants or modifications within the spirit of the invention.

In particular, although the bone anchoring portion 11 is described as being a hook, it could also be a screw such as a pedicle screw, inter alia.

We claim:

1. An implant for an osteosynthesis device, comprising:

an anchoring portion for anchoring to bone;

a body having a channel opening sideways in said body for receiving a rod and having a tapped hole, said channel sloping toward said anchoring portion from an outside portion thereof towards a center of said body;

a hollow cover fitting over and surrounding said body, said cover having a dome-shaped top portion with a opening extending therethrough and having two notches for receiving the rod on either side of said body, said opening facing said tapped hole; and a screw having a head bearing against said top portion of said cover and a threaded portion extending through said opening and threadedly engaged in said tapped hole in said body to affix said cover on said body.

2. An implant according to claim 1 wherein said body comprises a top portion which is hemispherical in shape; and said dome-shaped top portion of said cover has a hemispherical shape complimentary to said top portion of said body.

3. An implant according to claim 2 wherein said head of said screw comprises an outside surface with a curvature forming a continuation of said dome-shaped top portion of said cover.

4. An implant according to claim 1 wherein said head of said screw comprises an outside surface with a curvature forming a continuation of said dome-shaped top portion of said cover.

5. An implant according to claim 4 wherein said head of said screw comprises a socket for receiving and forming a torque transmitting connection with a tool.

6. An implant according to claim 1 wherein said head of said screw closes said opening in said cover.

7. An implant according to claim 1 wherein said tapped hole extends along a longitudinal axis of said body; and said channel extends generally transverse to said longitudinal axis.

8. An implant for an osteosynthesis device, comprising:

an anchoring portion for anchoring to bone;

a body having a channel opening sideways in said body and having a tapped hole, said channel sloping toward said anchoring portion from an outside portion thereof towards a center of said body;

a rod received in said channel;

a hollow cover fitting over said body and having a dome-shaped top portion terminating in a generally flat annular edge bearing against said rod adjacent longitudinal ends of said channel to lock said rod in said channel;

an opening in said top portion of said cover;

a tapped hole in said body facing said opening; and a screw having a head bearing against said top portion of said cover and having a threaded portion extending through said opening and threaded in said tapped hole to fix said cover on said body.

9. An implant according to claim 8 wherein said body comprises a top portion which is hemispherical in shape; and said cover comprises a cap having a hemispherical shape complementary to said top portion of said body.

10. An implant according to claim 9 wherein said head of said screw comprises an outside surface with a curvature forming a continuation of said hemispherical shape of said cap.

11. An implant according to claim 8 wherein said screw is fixed in said opening in said cover.

12. An implant according to claim 11 wherein said head of said screw comprises an outside surface with a curvature forming a continuation of said hemispherical shape of said cap.

13. An implant according to claim 8 wherein said head of said screw comprises an outside surface with a curvature forming a continuation of said hemispherical shape of said cap.

14. An implant according to claim 13 wherein said head of said screw comprises a socket for receiving and forming a torque transmitting connection with a tool.

15. An implant according to claim 8 wherein said head of said screw closes said opening in said cover.

16. An implant according to claim 8 wherein said tapped hole extends along a longitudinal axis of said body; and said channel extends generally transverse to said longitudinal axis.

\* \* \* \* \*